(12) United States Patent
Meyer et al.

(10) Patent No.: US 6,203,196 B1
(45) Date of Patent: Mar. 20, 2001

(54) X-RAY DIAGNOSTIC APPARATUS WITH A BEAM TRANSMITTER AND BEAM RECEIVER MOUNTED OPPOSITE ONE ANOTHER ON A CURVED HOLDER

(75) Inventors: Michael Meyer, Baiersdorf; Hans-Peter Seubert, Heroldsbach, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/377,751

(22) Filed: Aug. 20, 1999

(30) Foreign Application Priority Data

Sep. 1, 1998 (DE) .............................................. 198 39 825

(51) Int. Cl.[7] ...................................................... H05G 1/02
(52) U.S. Cl. ............................................ 378/197; 378/198
(58) Field of Search ..................................... 378/195–198

(56) References Cited

U.S. PATENT DOCUMENTS 3,549,885 * 12/1970 Andersson ........................... 378/197

5,661,772    8/1997 Bär et al. .

FOREIGN PATENT DOCUMENTS 89 05 588    10/1990 (DE) .
195 35 583    3/1997 (DE) .

* cited by examiner

Primary Examiner—Craig E. Church
(74) Attorney, Agent, or Firm—Schiff Hardin & Waite

(57) ABSTRACT

X-ray diagnostic apparatus has a beam transmitter and beam receiver mounted opposite one another on a curved holder. In a first operating mode, the curved holder is formed by at least a first circular ring segment on which the beam transmitter and the beam receiver are mounted. In a second operating mode, a second circular ring segment is coupled to the first circular ring segment so that a closed ring results. Displacement arrangements, as well as energy supply connections, are provided for the beam transmitter and the beam receiver, and a signal transmission arrangement for the beam receiver is provided, so that the beam transmitter and the beam receiver can be controlled, positioned opposite one another, so as to rotate around an examination subject. With this X-ray diagnostic apparatus, both transirradiation exposures and computed tomography exposures can be produced.

15 Claims, 16 Drawing Sheets

X-RAY DIAGNOSTIC APPARATUS WITH A BEAM TRANSMITTER AND BEAM RECEIVER MOUNTED OPPOSITE ONE ANOTHER ON A CURVED HOLDER

BACKGROUND OF THE INVENTION

1. Field of the Invention

The present invention is directed to an X-ray diagnostic apparatus of the type having a beam transmitter and a beam receiver mounted opposite one another on a curved holder.

2. Description of the Prior Art

An X-ray diagnostic apparatus of the above type is known, for example, as a ceiling-mounted or floor-mounted apparatus from German Utility Model 89 05 588, and as a mobile apparatus from German PS 195 35 583. In particular, these X-ray diagnostic apparatuses have a C-arm-type holder that can be displaced on a mount along its circumference, and can be displaced around a horizontal axis, as well as also in the vertical direction if necessary. In this way, X-ray examinations can be carried out from various irradiation directions.

German OS 197 11 499 discloses an X-ray diagnostic apparatus with a CT means and with an X-ray transirradiation means. With this X-ray diagnostic apparatus, transillumination examinations, angiography examinations, and computed tomography examinations can be carried out.

Computed tomography apparatuses have a cube-like gantry with a center opening in which an examination subject can be arranged so that the subject can be examined using X-ray radiation. Accessibility to the subject is not possible, or is at least hindered. If a repositioning of the subject is required, displacement must take place out of the gantry, followed by repositioning and reintroduction into the gantry.

If both angiography and computed tomography examinations are required, in the most advantageous case a computed tomography apparatus and an angiography apparatus are arranged in the same examination room. A repositioning of the subject from the computed tomography apparatus to the angiography apparatus must however still be carried out. A possibility for avoiding this repositioning is disclosed in the aforementioned German OS 197 11 499. It is often the case, however, for the computed tomography apparatus and the angiography apparatus to be arranged in different rooms, so that not only a repositioning but also a transporting of the subject is required.

SUMMARY OF THE INVENTION

An object of the present invention is to provide an X-ray diagnostic apparatus of the type initially described wherein both transirradiation examinations and computed tomography examinations can be carried out.

This object is achieved in accordance with the principles of the present invention in an X-ray diagnostic apparatus having, in a first operating mode, in particular a transirradiation mode, a curved holder with at least one first circular ring segment on which the beam transmitter and beam receiver are mounted. In this operating mode, the X-ray diagnostic apparatus, and in particular the curved holder that is open at one side, can be oriented—particularly if it is constructed as a C-arm—with the beam transmitter and the beam receiver to the subject under examination for transirradiation from various directions. In a second operating mode, in particular a computed tomography mode, a second circular ring segment is combined with the first circular ring segment so that a closed ring results. A subject can be arranged inside the closed ring. Displacement means, as well as an energy supply for the beam transmitter and beam receiver, as well as a signal transmission system allocated to the beam receiver, are provided, and the beam transmitter and the beam receiver can be driven, positioned opposite one another, in rotation around the subject. The signals emanating from the beam receiver corresponding to radiation incident during an examination of the subject can be supplied to a computing unit for display at a monitor as a transirradiation image. As a result, with an inventive X-ray diagnostic apparatus both transirradiation exposures and computed tomography exposures are possible, without requiring a repositioning of the subject, or transportation into another examination room. Such an X-ray diagnostic apparatus can be used with particular advantage in the operating room, since it occupies little space and nonetheless enables both transirradiation exposures and computed tomography exposures.

It is advantageous for the first and second circular ring segments to be mounted on respective mount apparatuses, and for the mount apparatuses to permit coupling and decoupling of the circular ring segments by means of a corresponding displacement. The X-ray diagnostic apparatus thus can be converted in a simple and economical manner from a transirradiation apparatus into a computed tomography apparatus, and vice versa.

In order to increase the displaceability of the X-ray diagnostic apparatus, it is particularly advantageous for the second circular ring segment to be decouplable from its mount apparatus.

In order also to enable examinations from various directions, it is advantageous for the mount apparatus of the first ring segment and/or of the second ring segment to be spatially displaceable.

The design of an inventive X-ray diagnostic apparatus is particularly advantageous when the second circular ring segment can be displaced on the first circular ring segment so as to form a closed ring. A separate mount apparatus for the second circular ring segment thus can be foregone.

In this version it is particularly advantageous for the second circular ring segment to be adjusted on the first circular ring segment in a telescoping arrangement.

In a further embodiment of the inventive X-ray diagnostic apparatus, the second circular ring segment can be pivoted around an axle on the first circular ring segment, so that a complete ring can be formed. This particularly facilitates easy use of the X-ray diagnostic apparatus both as a transirradiation apparatus and as a computed tomography apparatus.

In another embodiment of the X-ray diagnostic apparatus according to the invention, end extensions are provided on an additional curved holder, these extensions being constructed as rails or as a telescoping assembly and allow the beam transmitter and the beam receiver to be displaced, in the range of displacement of the extension, away from a third mount apparatus for the additional curved holder or toward this third mount apparatus. The third mount apparatus can enable rotation of the additional curved holder around an axis of rotation, so that besides transirradiation exposures it is also possible to produce computed tomography exposures during a rotation, and in addition a larger area of the subject can be scanned using the extensions.

The inventive X-ray diagnostic apparatus can be displaceable on ceiling rails and/or on floor rails or via a carriage or cart that can be moved freely.

DESCRIPTION OF THE PREFERRED EMBODIMENTS

Figure 1:
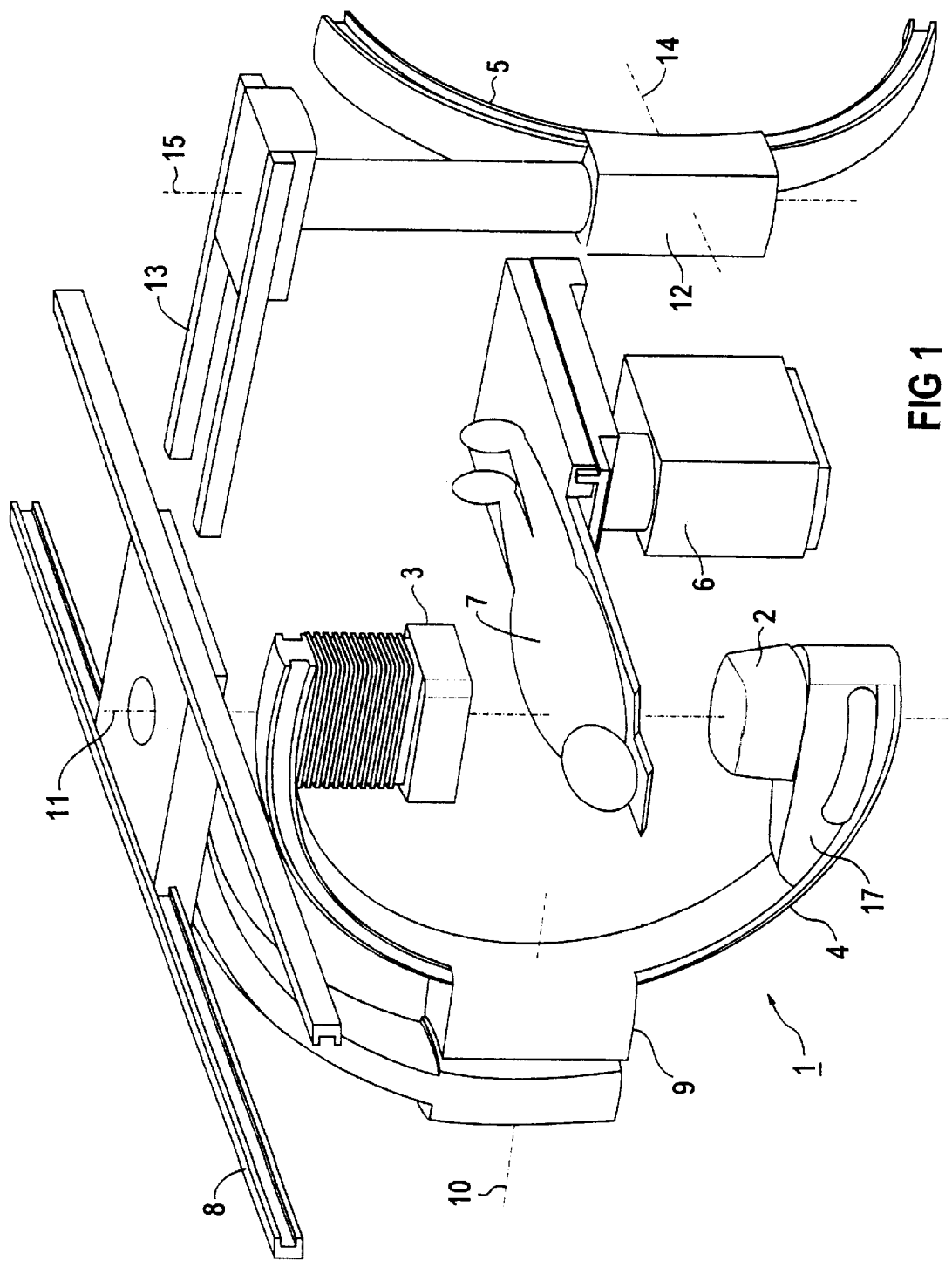
FIG. 1 shows a first embodiment of an X-ray diagnostic apparatus according to the invention, with a decoupled second circular ring segment.

The figures show an X-ray diagnostic apparatus in various embodiments having a curved holder 1, a beam transmitter 2, a beam receiver 3, a first circular ring segment 4, a second circular ring segment 5. Inessential to the invention, but shown nonetheless, are a mount apparatus 6 for an examination subject 7, as well as ceiling rails on which the curved holder 1 can be spatially displaced. The curved holder 1 is preferably capable of being displaced on a first mount apparatus 9 along its circumference, as well as around a horizontal axis 10 and a vertical axis 11.

In the embodiment of the invention according to FIG. 1, the second circular ring segment 5 is mounted on a second mount apparatus 12 and can be displaced on additional ceiling rails 13. Preferably, the second circular ring segment 5 also can be displaced around an additional horizontal axis 14 and around an additional vertical axis 15. In the state shown in FIG. 1, the second circular ring segment 15 is in a standby (parked) position, in which it does not interfere luring the examination of the subject 7. Transirradiation exposures thus can be produced with the X-ray diagnostic apparatus from various projection directions.

Figure 2:
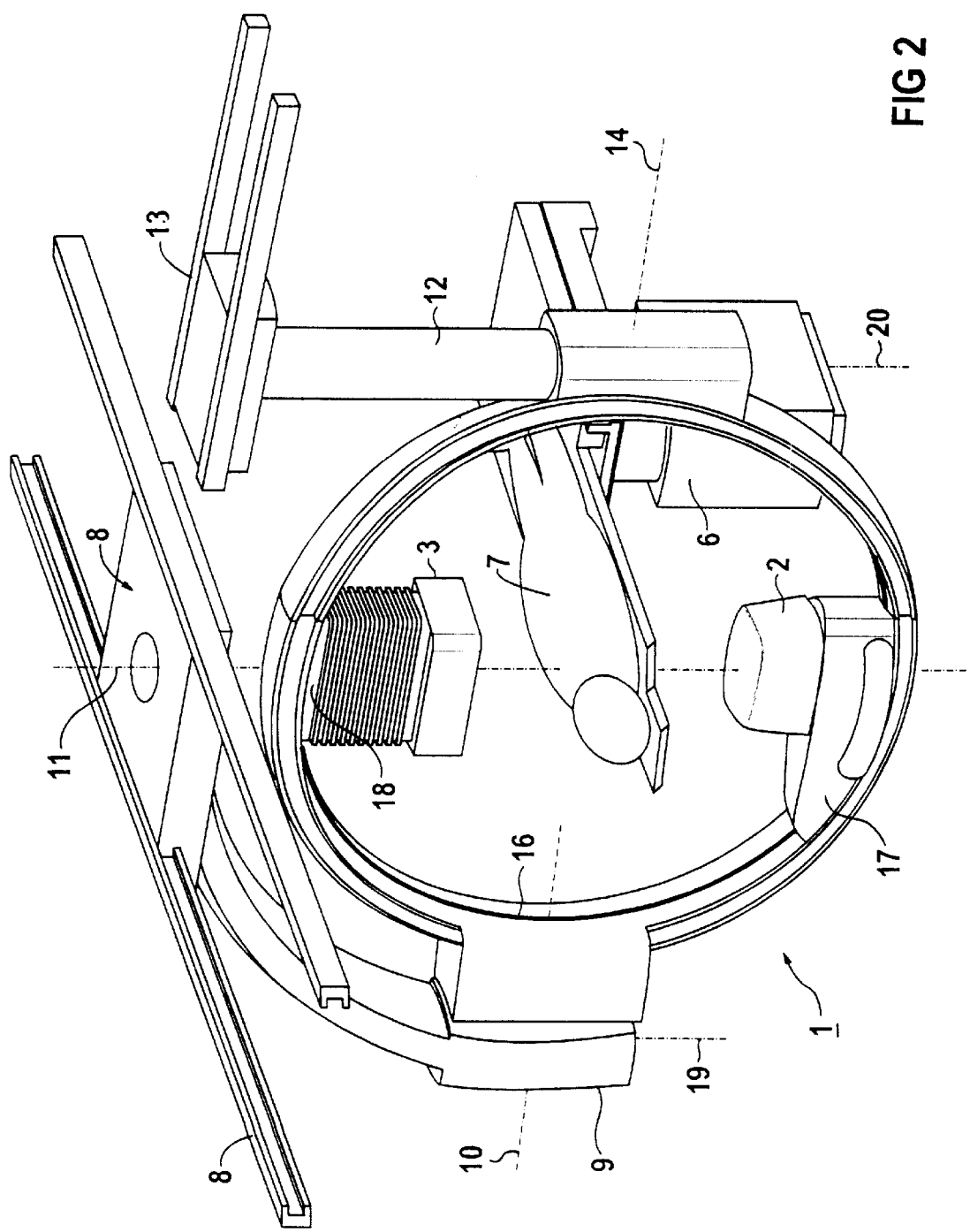
FIG. 2 shows the X-ray diagnostic apparatus according to FIG. 1, with a coupled second circular ring segment.

FIG. 2 shows that, by means of the second mount apparatus 12, the second circular ring segment 5 can be brought into a position in which it is coupled to the first circular ring segment 4. Both a mechanical and an electrical coupling of the first and second circular ring segments 4, 5 takes place. A mechanical coupling can take place by means of correspondingly fashioned profile parts that engage with one another in a positively locking fashion. An electrical coupling can take place via plug-socket couplings or direct blunt coupling of current rails or plugs.

Figure 4:
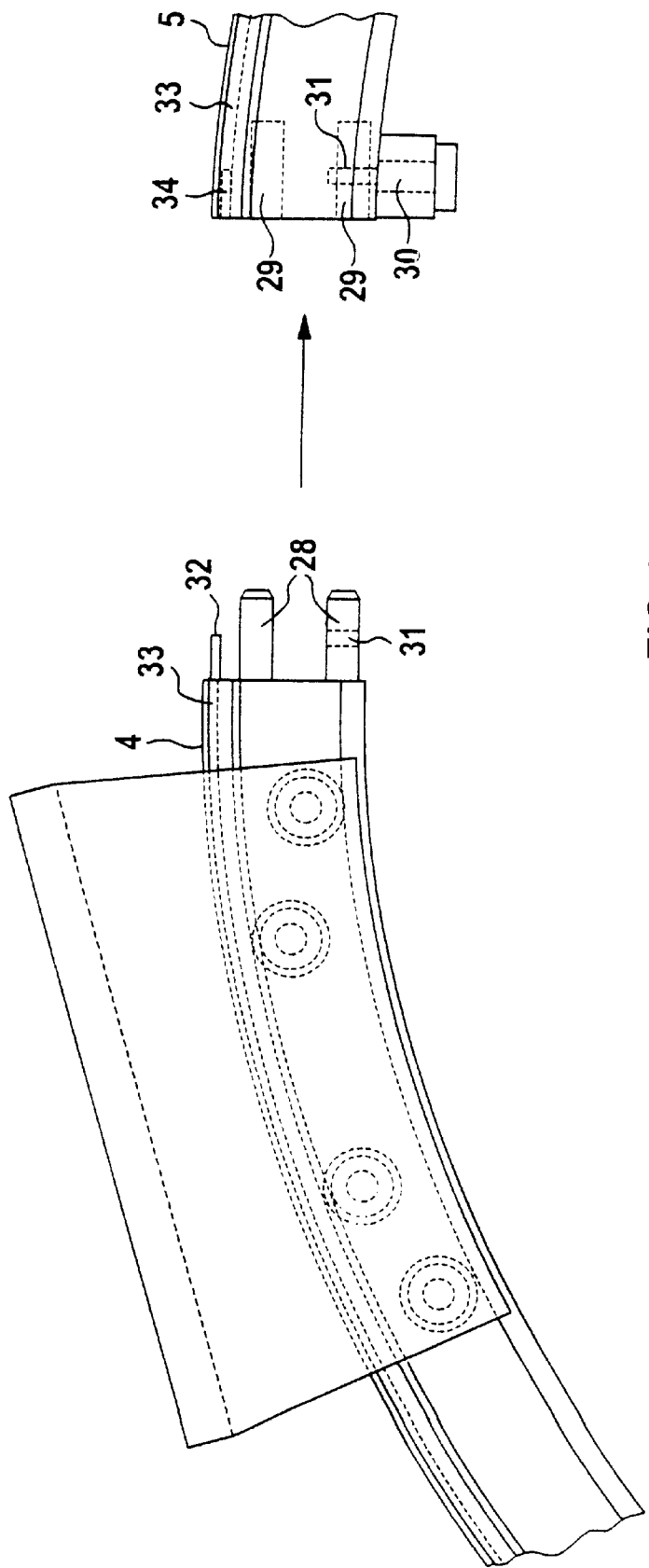
FIG. 4 shows an embodiment of a mechanical and electrical coupling of the circular ring segments of the X-ray diagnostic apparatus according to FIGS. 1 to 3.

FIG. 4 shows an example wherein mechanical pins 28 are fashioned on the first circular ring segment 4, these pins 28 engaging in openings 29 provided on the second circular ring segment 5 in the coupled state. For the mechanical arresting of the circular ring segments 4, 5 with one another, a bolt 30 can be provided that leads, in the locked state, through a bolt opening 31 of at least one mechanical pin 28. Within the scope of the invention, this bolt 30 can of course also be displaced electromechanically, e.g. by an electromagnet. FIG. 4 also shows a plug 32 connected with a current rail 33 provided on the first circular ring segment 4. As a counterpiece, a socket 34 is provided on the second circular ring segment 5, the socket 34 being connected with a current rail 33 of the second circular ring segment 5, and in which the plug 32 engages when the circular ring segments 4, 5 are coupled. Each circular ring segment 4, 5 is fashioned so that at least one guide rail 16 is provided thereon. On this guide rail 16, via a carriage 17, the beam transmitter 1 is displaced, and via an additional carriage 18 the beam receiver 2 can be displaced, opposite one another, on the ring formed by the first and second circular ring segments 4, 5 (FIG. 2, 3). The energy for the production of a beam bundle can be supplied to the beam transmitter 1 via the electrical contacts. During the examination of the subject 7, the beam receiver 3 receives the beam bundle that penetrates the subject 7, and converts the intensity of the incident radiation into electrical signals that can be supplied to a computer via a signal transmission means for evaluation. On the basis of these signals, transirradiation images and/or computed tomography images can be produced in a known manner via the computer.

Figure 3:
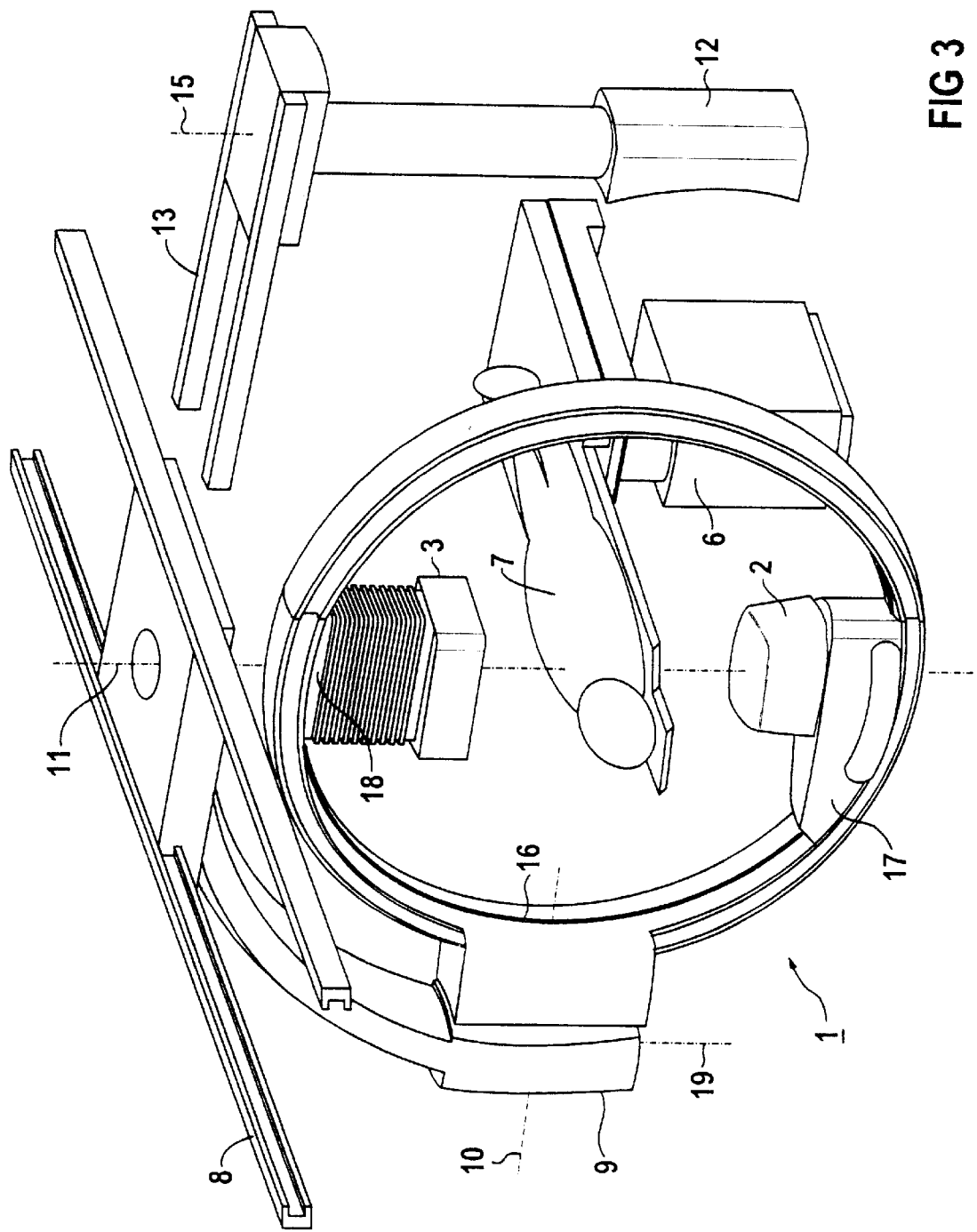
FIG. 3 shows the X-ray diagnostic apparatus according to FIGS. 1 and 2 with a mount apparatus decoupled from the second circular ring segment.

In an embodiment, the ring formed by the first and second circular ring segments 4, 5 can be pivoted around the horizontal axes 10, 14, which coincide in the coupled state, so that computed tomography exposures can also be produced from various directions of transirradiation. It is particularly advantageous for the first circular ring segment 4 to be pivotable around a vertical axis 19 of the first mount apparatus 9 and the second circular ring segment 5 to be pivotable around a vertical axis 20 of the second mount apparatus 12. In connection with the displaceability of the first and second mount apparatuses 9, 12 along the ceiling rails 8, 13, the ring formed by the first and second circular ring segments 4, 5 also still can be pivoted around the vertical axis 11, which advantageously creates another projection possibility for the production of computed tomography exposures. The coupling of the first and second circular ring segments 4, 5 to the second mount apparatus 19 increases the stability against oscillations that can occur during the rotation of the beam transmitter 1 and of the beam receiver 3. However, within the scope of the invention it is also possible to decouple the second circular ring segment 5 from the mount apparatus 12 (FIG. 3), which improves access to the subject 7. However, the first mount apparatus 9 must then be dimensioned to ensure an oscillation-free rotation of the beam transmitter 1 and beam receiver 3.

Figure 5:
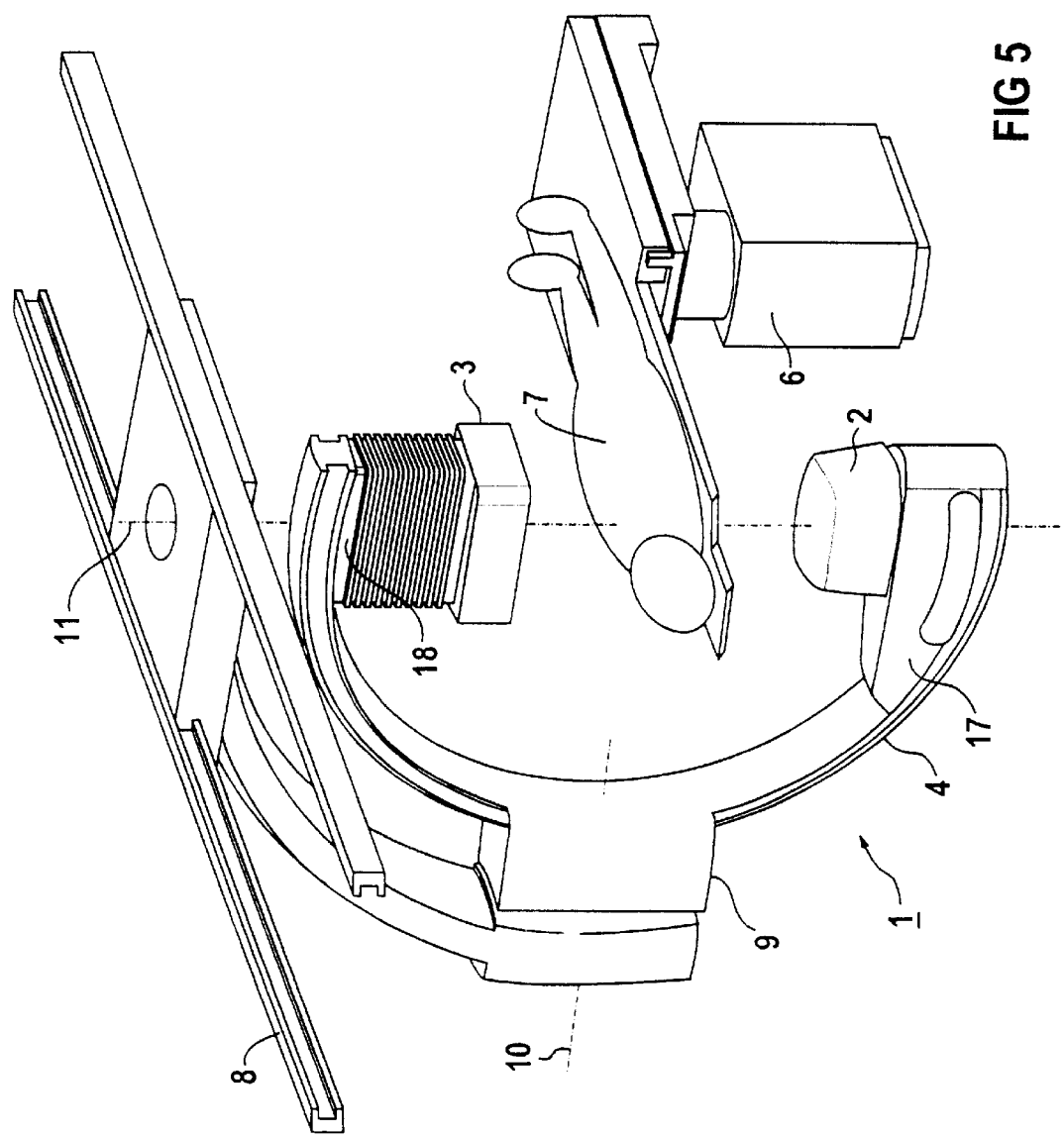
FIG. 5 shows a second embodiment of an X-ray diagnostic apparatus according to the invention, with a second circular ring segment that can be displaced in telescopic fashion on the first circular ring segment.
Figure 6:
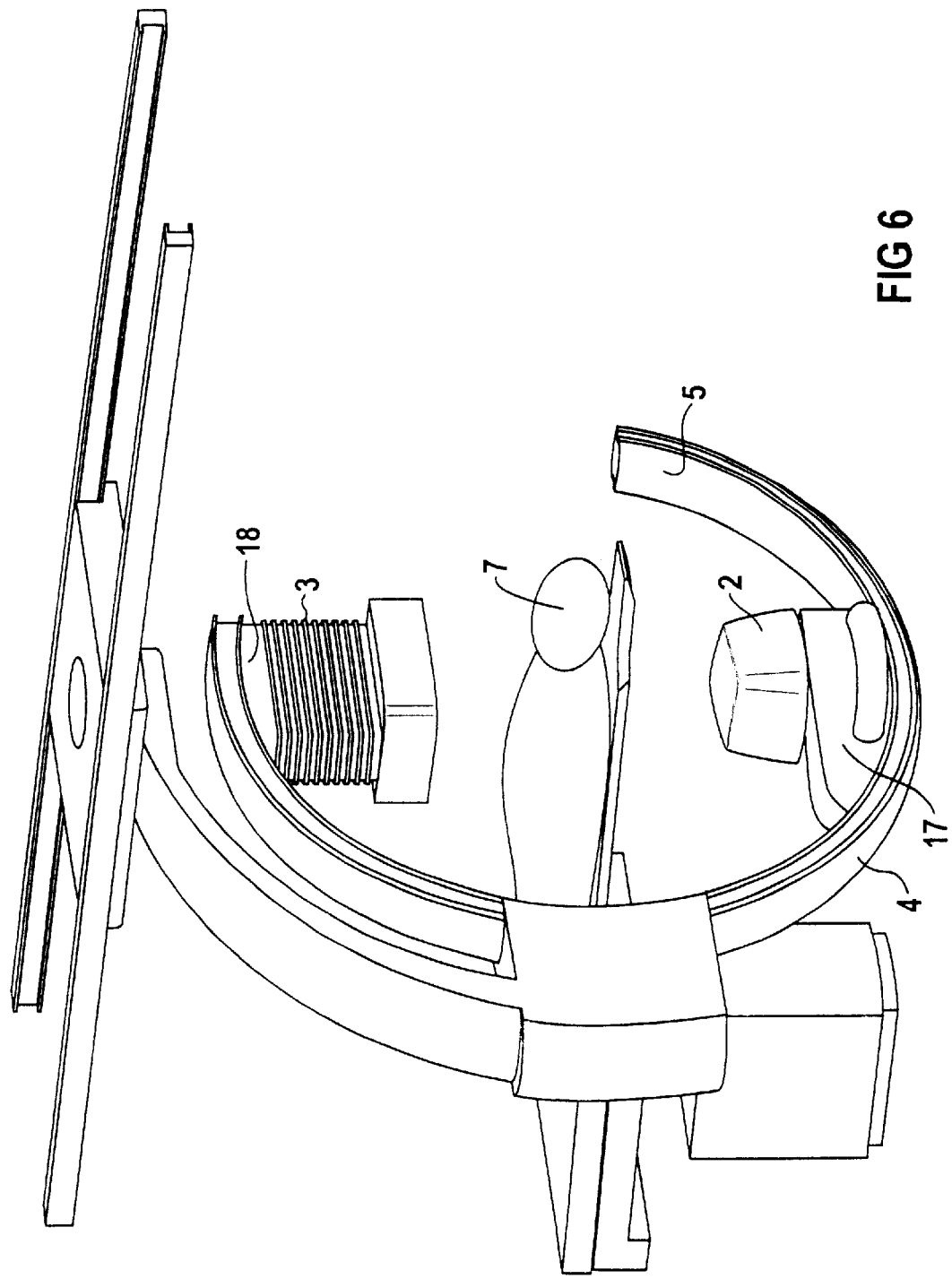
FIG. 6 shows the X-ray diagnostic apparatus according to FIG. 5, with a second circular ring segment partially displaced on the first circular ring segment.
Figure 7:
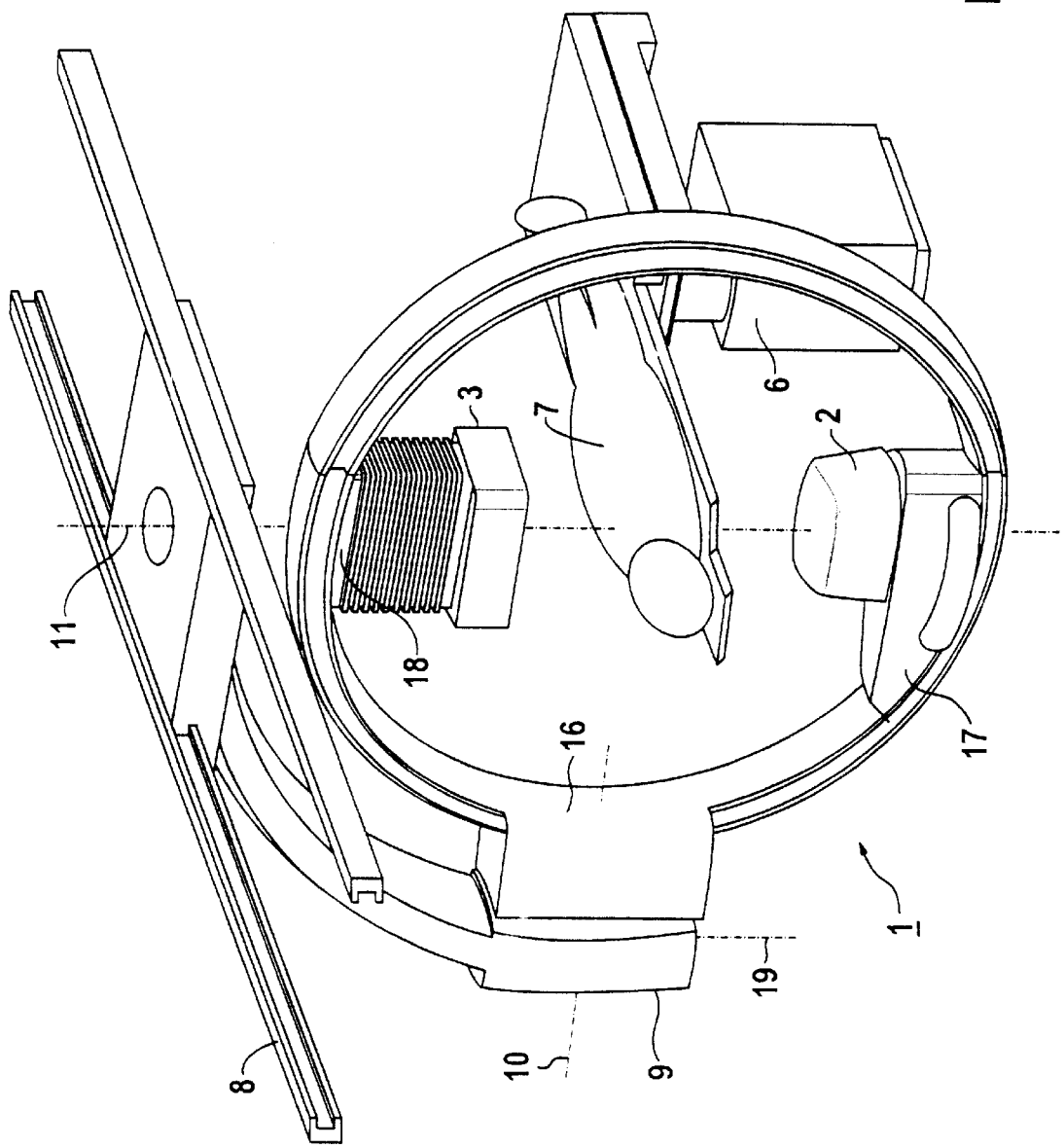
FIG. 7 shows the X-ray diagnostic apparatus according to FIG. 5 with a ring formed from the first and second circular ring segment.
Figure 8:
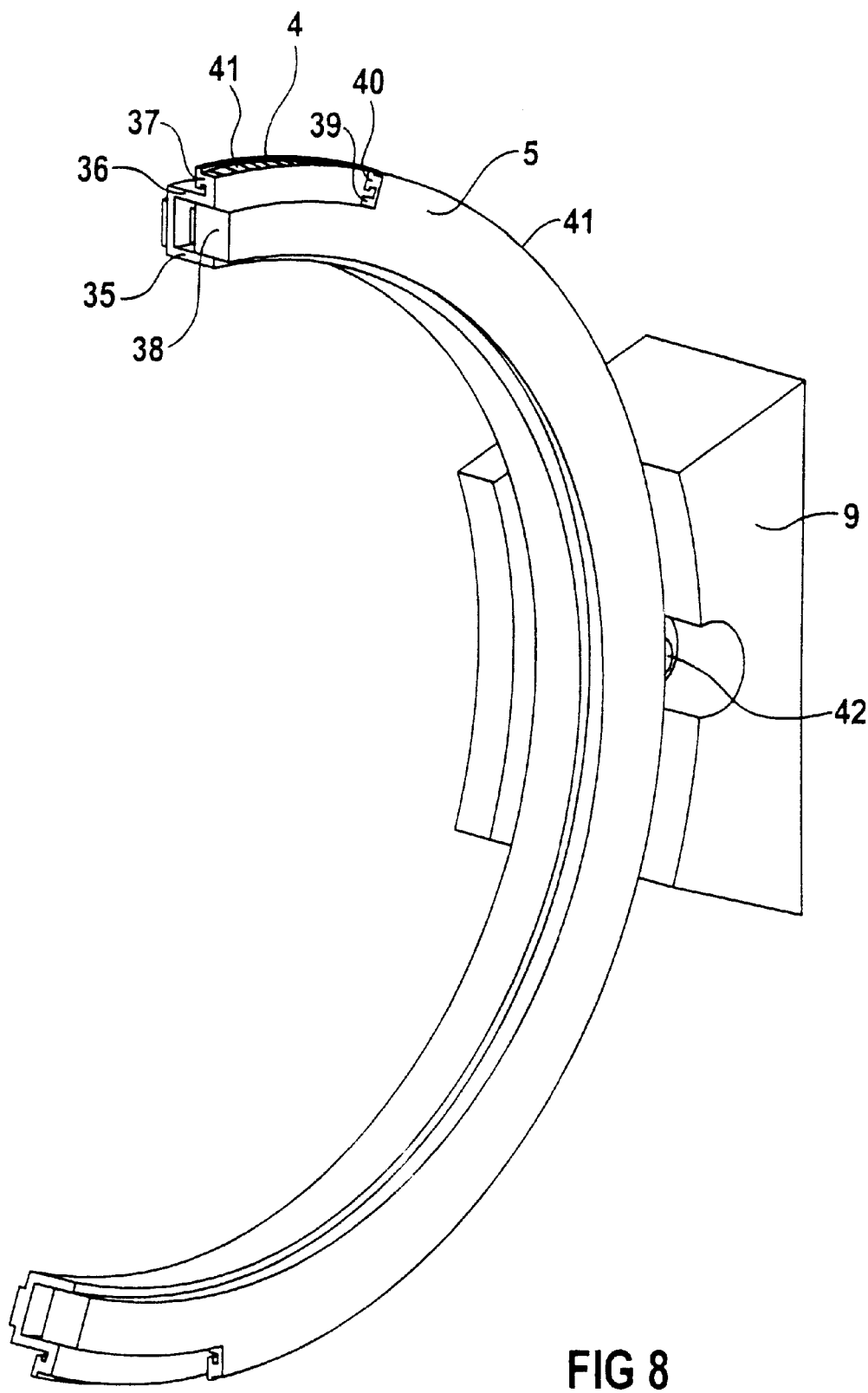
FIG. 8 shows a profile of the X-ray diagnostic apparatus according to FIGS. 5 to 7.

FIGS. 5 to 7 show a second embodiment of an X-ray diagnostic apparatus according to the invention, in which, in contrast to the embodiment according to FIG. 1, the second circular ring segment 5 is mounted displaceably, in telescoping fashion, on the first circular ring segment 4. As shown in FIGS. 6 and 7, the second circular ring segment 5 thus can be adjusted so that it forms a closed ring with the first circular ring segment 4, on which closed ring the beam transmitter 1 and the beam receiver 3 can rotate. For this purpose, the second circular ring segment 5 can be constructed of one piece, and can be received by the first circular ring segment 4. Preferably, however, the second circular ring segment 5 has several parts, preferably two, with a first part arranged close to the beam transmitter 2 and a second part arranged close to the beam receiver 3. Shorter adjustment paths thus result, but more contact points must be provided. In comparison to the first embodiment of the X-ray diagnostic apparatus according to the invention, no second mount apparatus 12 needs to be provided, but a considerably higher constructive outlay is required with regard to the adjustability of the second circular ring segment 5 on the first circular ring segment 4.

Details of an embodiment of a profile of the X-ray diagnostic apparatus according to FIGS. 5 to 7 as shown in FIGS. 8 to 11. Here the first circular ring segment 4 has a first part 35 with an approximately U-shaped cross-section, and a second part 36 that is approximately L-shaped, with the long leg of the L-shaped part 36 and one limb of the U-shaped part 35 forming the same part of the profile. At its end, the short leg of the L-shaped part 36 proceeds into a part 37 that is at least approximately T-shaped, the 37 part serving, on the first mount apparatus 9, to guide the first circular ring segment 4. In this embodiment, the second circular ring segment 5 has a region 38 with an approximately quadrangular cross-section, which is received at least partially in the U-shaped part 35. An additional part 39 that is approximately L-shaped is connected with the quadrangular region 38, to which an additional at least approximately L-shaped part 40, similar to that of the first circular ring segment 4, is likewise connected at the end. A toothed ring 41 can be fashioned on the outwardly oriented long leg of the T-shaped parts 37, 40, this ring 41 meshing with a toothed wheel 42 that is connected with a drive, in order to effect a displacement of the circular ring segments 4, 5 along the circumference thereof. A conveyor drive or friction roller drive is also suitable for this purpose, with equivalent action. For the displacement of the second circular ring segment 5 along the circumference thereof for forming a closed ring with the first circular ring segment 4, a second drive (not shown) can be provided with a toothed wheel also engaging the toothed ring 41. Current rails 43 can be fashioned on the short leg of the L-shaped parts 36, 39, these rails 43 serving for voltage supply and signal transmission. It goes without saying that the first mount apparatus 9 has mounting elements for both the first and the second circular ring segments 4, 5, which are known in the prior art and can be, for example, guide rollers.

Figure 9:
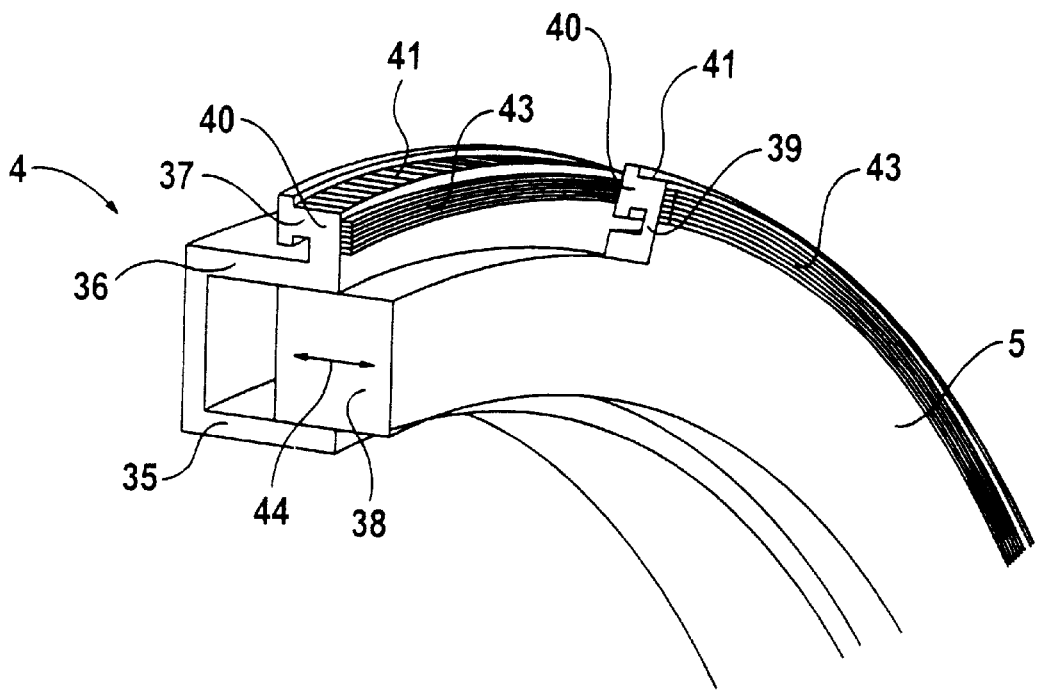
FIG. 9 shows an enlarged profile representation according to FIG. 8.
Figure 11:
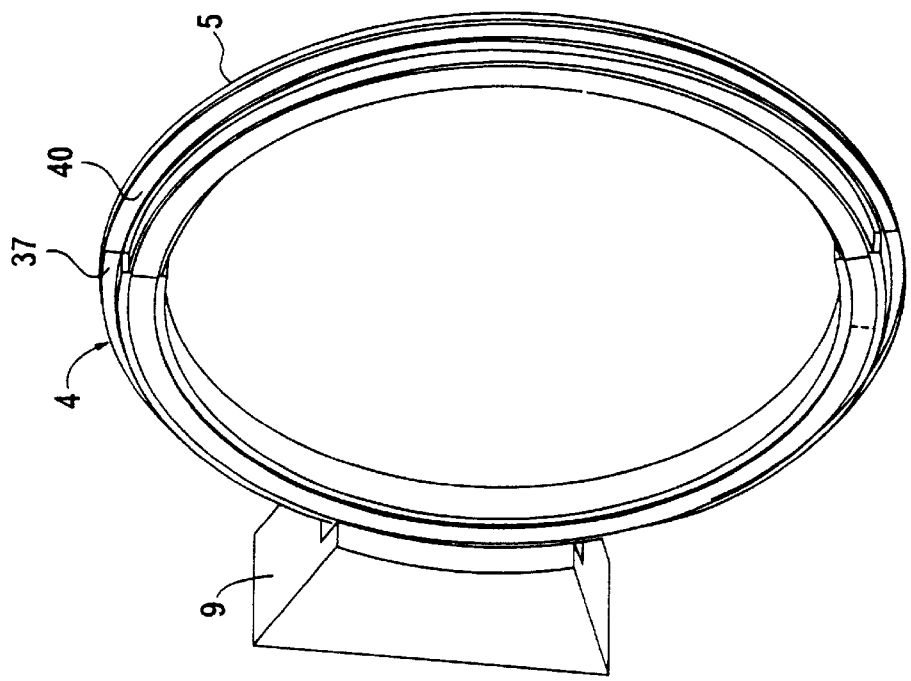
FIG. 11 shows the profile of the X-ray diagnostic apparatus according to FIG. 7 in a second side view.
Figure 10:
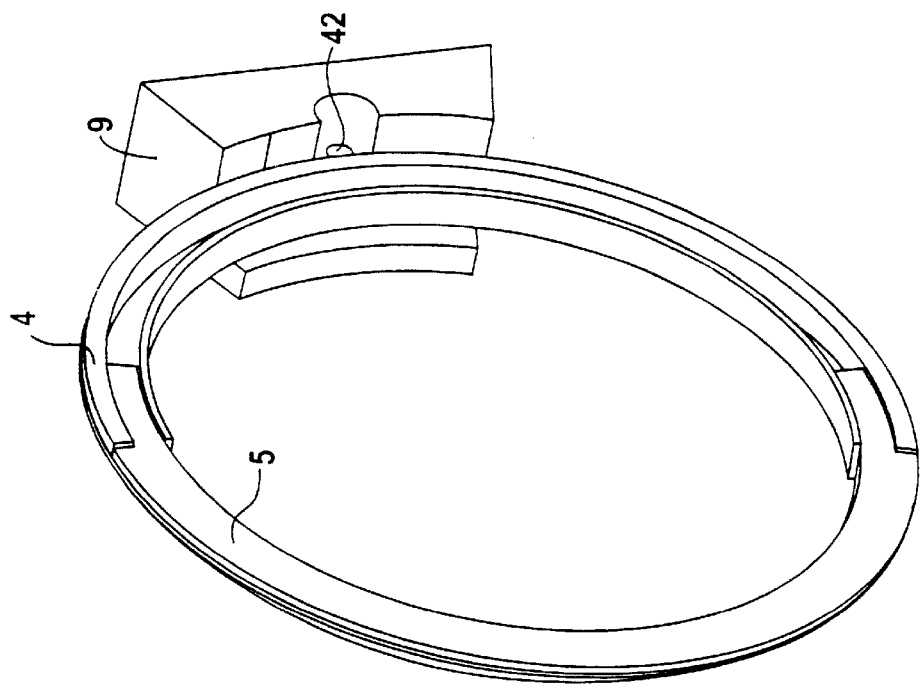
FIG. 10 shows the profile of the X-ray diagnostic apparatus according to FIG. 7 in a first side view.

When the first and second circular ring segments 4, 5 are displaced for the formation of a ring according to FIGS. 10 and 11, in the end position there results a relative displacement of the circular ring segments 4, 5 relative to one another such that the T-shaped parts 37, 40 and the current rails 43 are connected to one another in an approximately seamless fashion. In FIG. 9, the arrow 44 indicates that, for example, the second circular ring segment 5 can be displaced in the direction towards the first circular ring segment 4. Using means not shown, which engage the second circular ring segment 5 e.g. via a lever arrangement provided in the first mount apparatus 9, this second segment 5 can be removed from the first circular ring segment 4, and thus again can be displaced in telescoping fashion on the first circular ring segment 4 in order to form a C-arm. Instead of a lever arrangement, an electromechanical means can be used that is supported and operated between the first circular ring segment 4 and the second circular ring segment 5, which displaces the first circular ring segment into the right position shown in FIG. 9. At the end (not shown in FIG. 9) of the first circular ring segment 4, an opening can be formed for the quadrangular region 38, which opening, fashioned for example as an oblique guide, guides the facing end of the second circular ring segment 5 in the direction toward the first circular ring segment 4.

Figure 12:
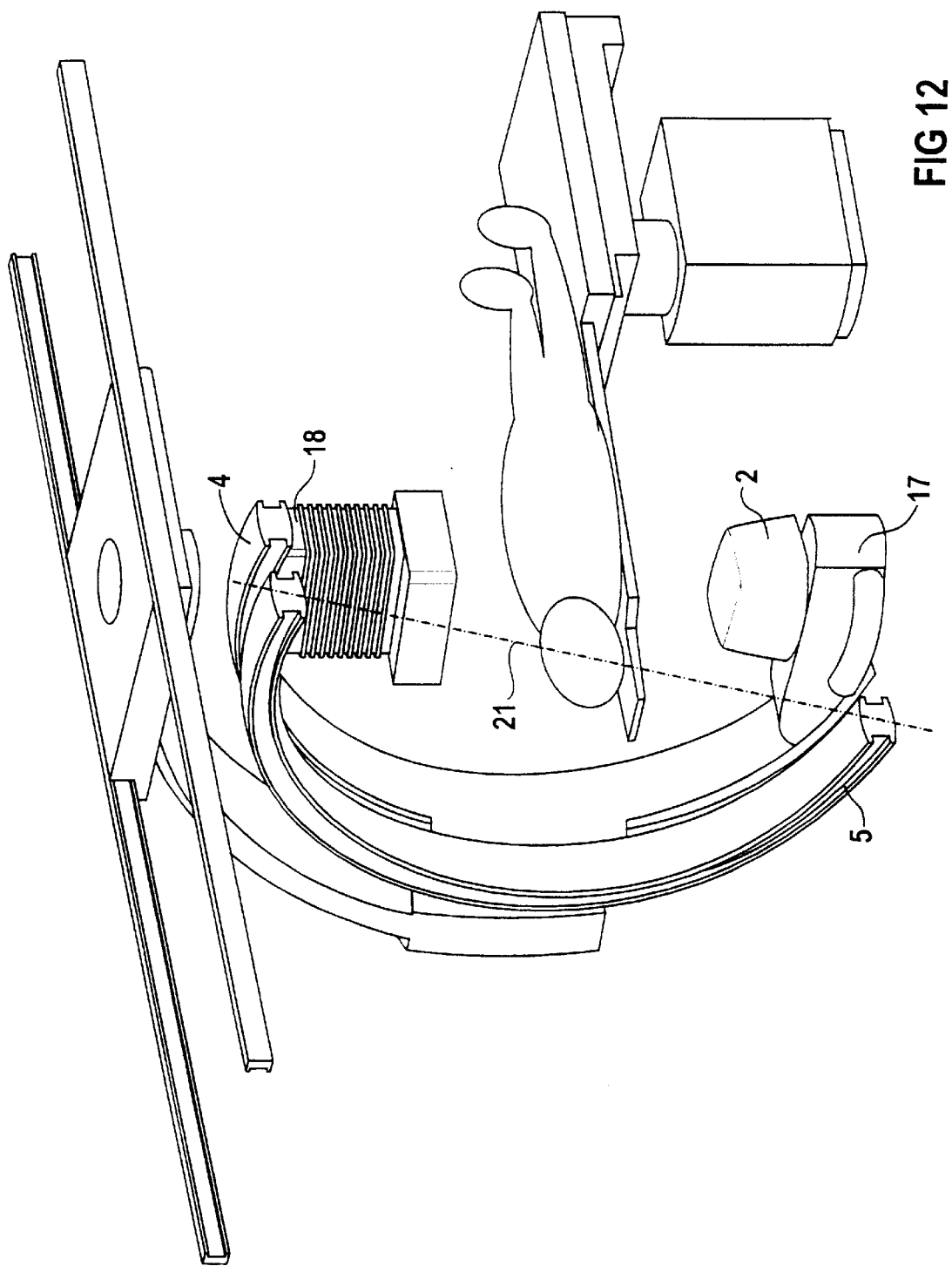
FIG. 12 shows a third embodiment of an X-ray diagnostic apparatus according to the invention, with a second circular ring segment mounted pivotably on an axis.
Figure 13:
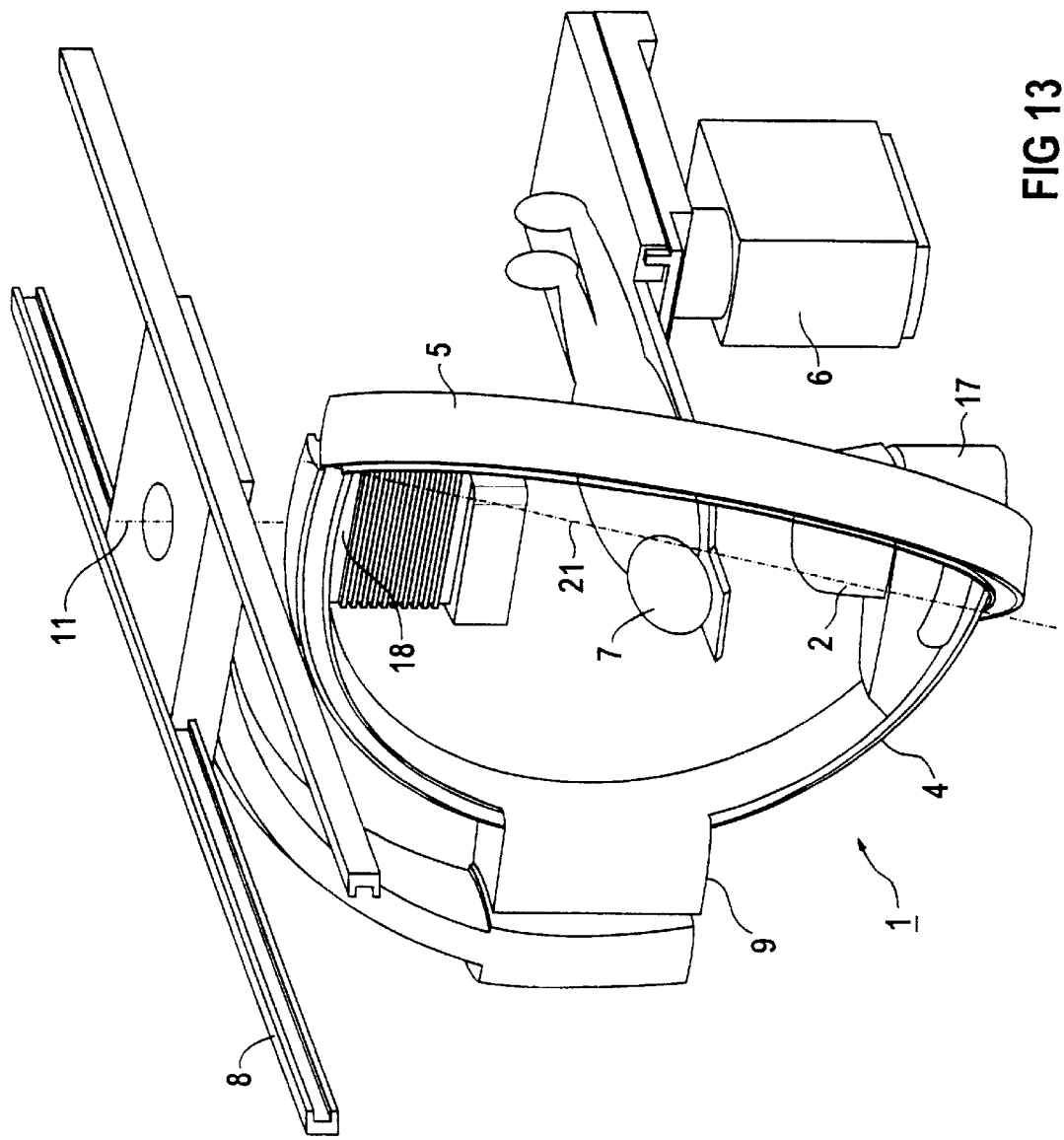
FIG. 13 shows the X-ray diagnostic apparatus according to FIG. 12 with a circular ring segment pivoted partially around the axis.
Figure 14:
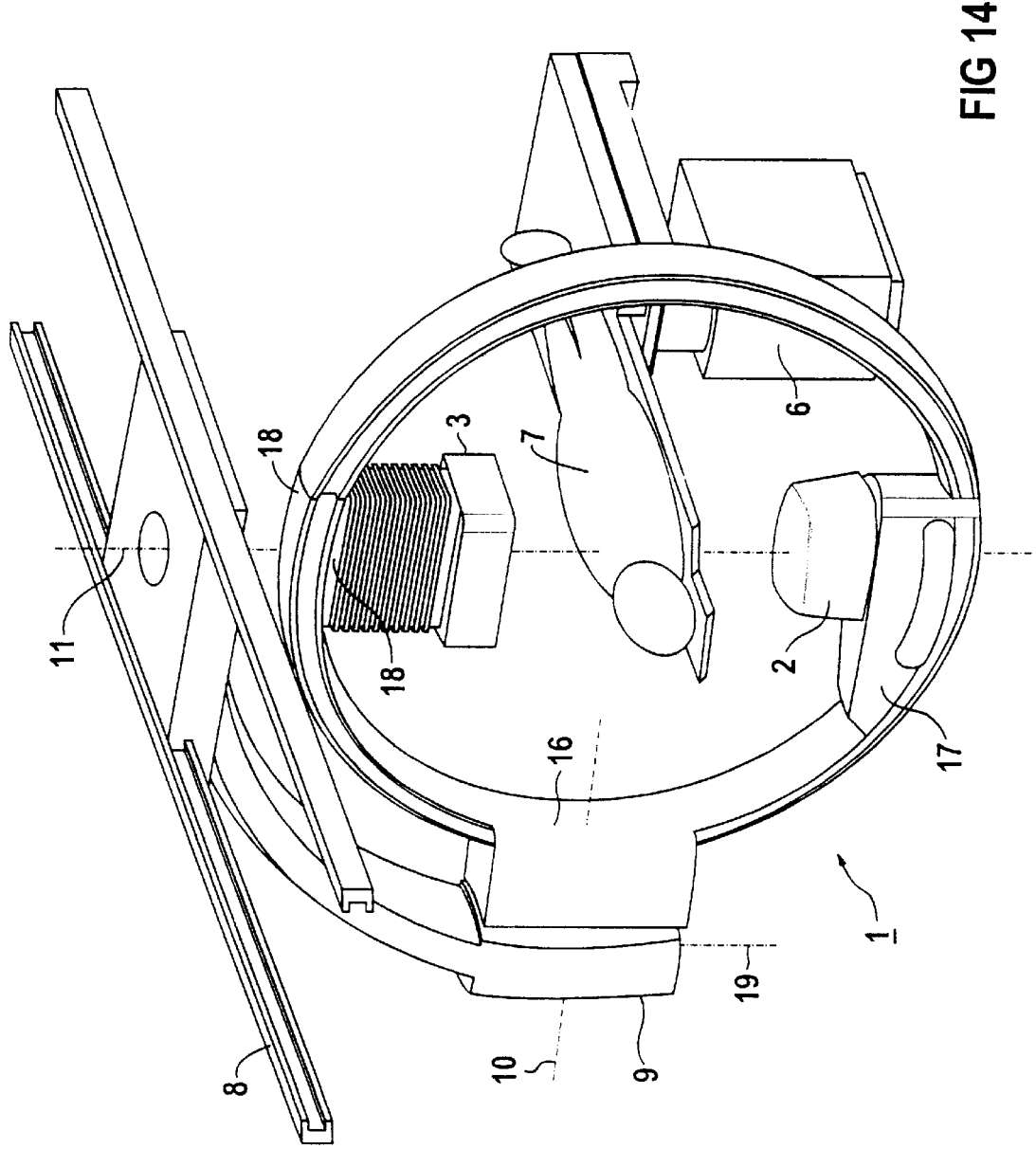
FIG. 14 shows the X-ray diagnostic apparatus according to FIG. 12, with a ring formed by the first and second circular ring segment.

FIGS. 12 to 14 show a variant of the invention in which it is possible to do without a second mount apparatus 12 according to the embodiment according to FIG. 1 and without an increased constructive outlay according to the embodiment according to FIG. 2. The second circular ring segment 5 on the first circular ring segment 4 in this version can be pivoted on the first circular ring segment around an axis of rotation 21, so that it can be pivoted according to FIG. 13 from an orientation—shown in FIG. 12—parallel to the first circular ring segment 4, and, as shown in FIG. 14, can be coupled with the first circular ring segment 4 for the formation of a ring. If the pivot bearings of the axis of rotation 21 are of detachable construction, the second circular ring segment 5 can be decoupled if necessary.

Within the scope of the invention, according to the embodiments shown in FIGS. 1 to 14 the beam transmitter 1 and the beam receiver 3 also can be coupled with the first circular ring segment 4 directly, omitting the respective carriage 17, 18. For displacement, a drive is then provided on the first mount apparatus 9 by means of which the ring formed by the first and second circular ring segments 4, 5 can be displaced along its circumference. In a computed tomography mode, the first and second circular ring segments 4, 5 then can rotate around an isocenter, together with the beam transmitter 1 and the beam receiver 3. The supply of energy and/or signal transmission can hereby take place via slip ring contacts in connection with electrical rails, via cables, or by means of inductive and/or capacitive transformers.

Figure 15:
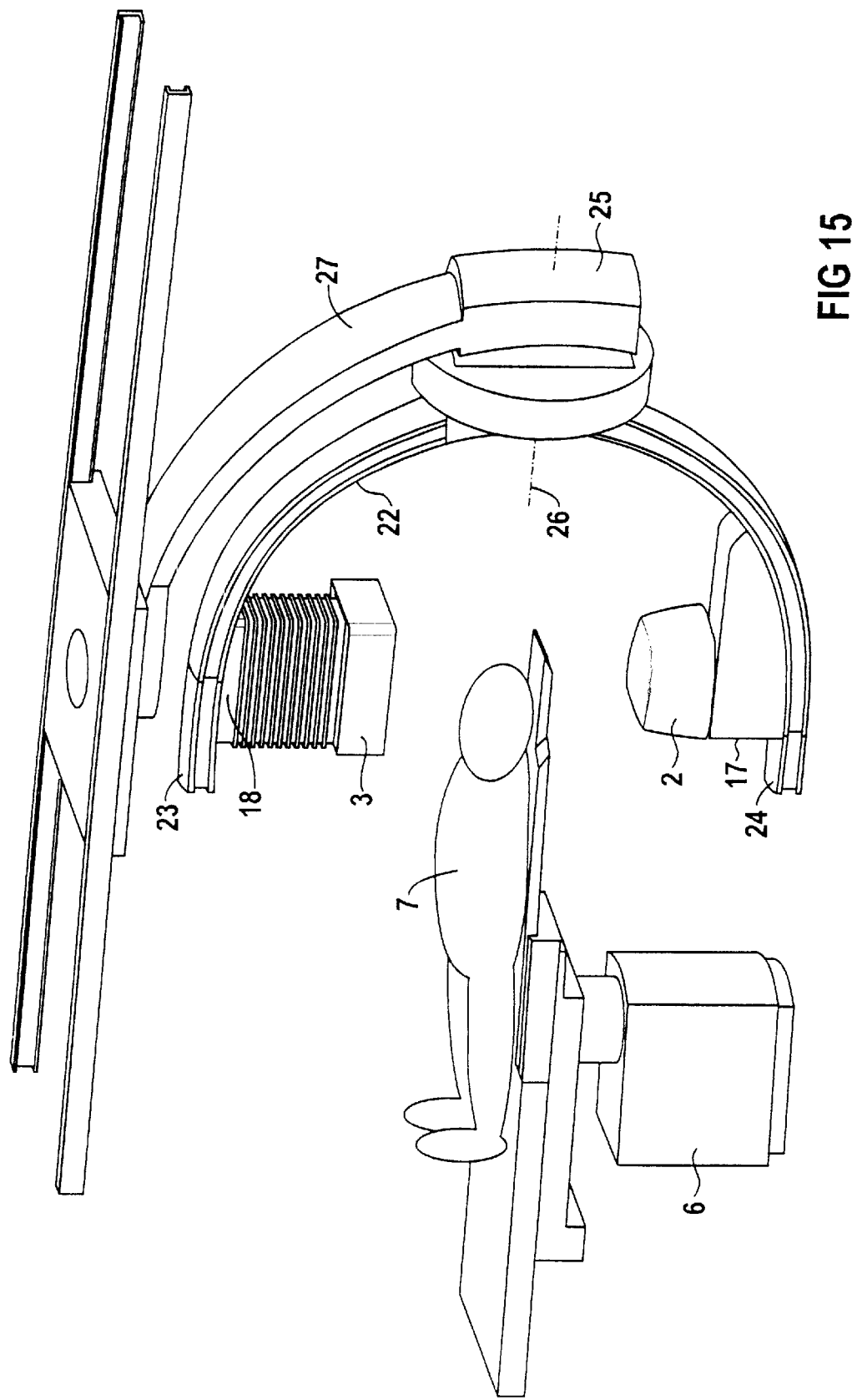
FIGS. 15 and 16 show a fourth embodiment of an X-ray diagnostic apparatus according to the invention with extensions provided at the ends on the curved holder.
Figure 16:
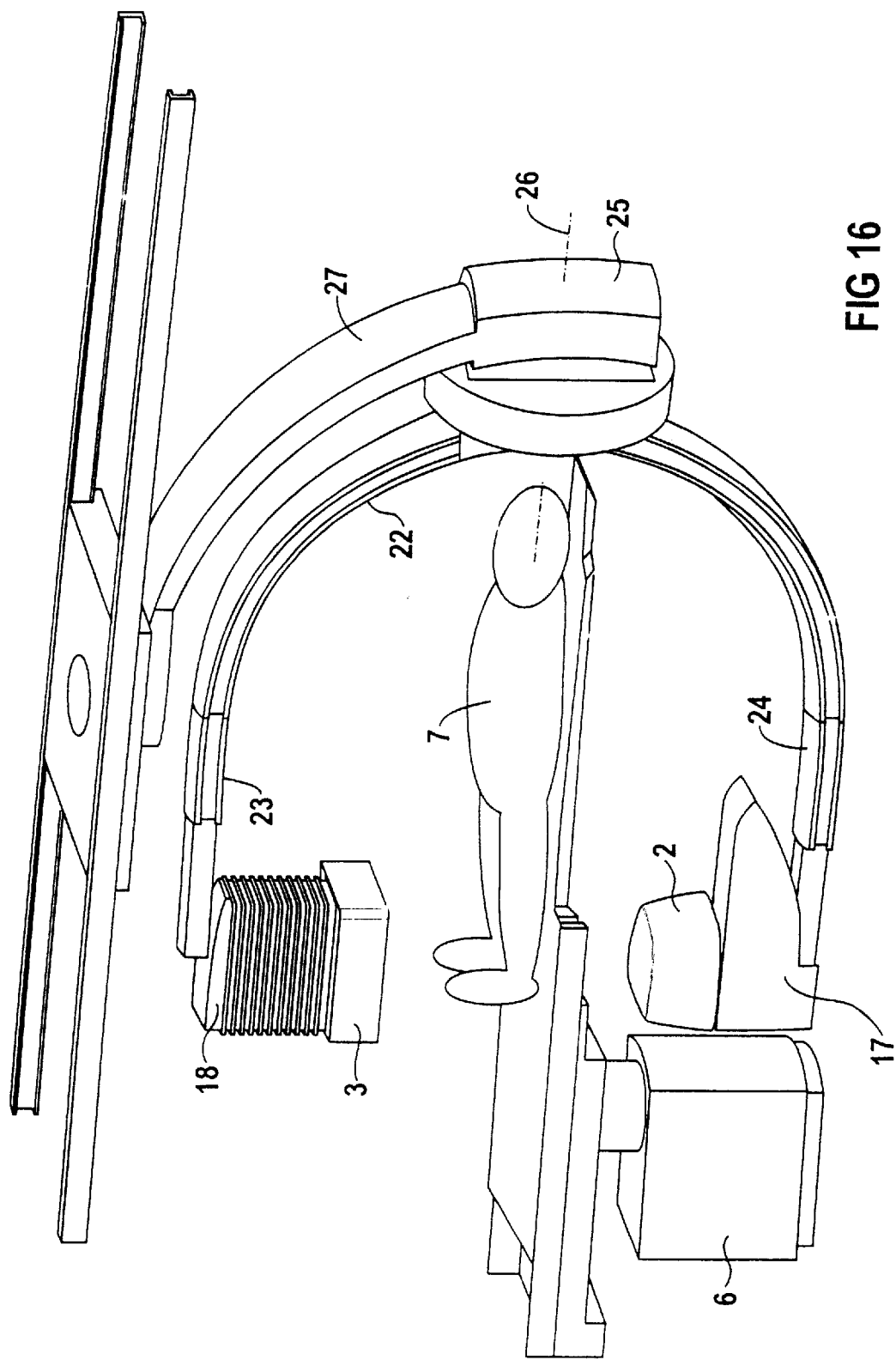

In a further variant of the invention according to FIGS. 15 and 16, extensions 23, 24 are respectively provided at the ends of a curved holder 22, these extensions 23, 24 being in the form of rails (FIG. 15) or telescoping elements (FIG. 16). The extensions 23, 24 make it possible to displace the beam transmitter 1 and the beam receiver 3, in the range of displacement of the extensions 23, 24, away from a third mount apparatus 25 for curved holder 22 or towards this holder 22. The third mount apparatus 25 enables the rotation of the curved holder 22 around an axis of rotation 26, so that computed tomography exposures can also be produced with such an X-ray diagnostic apparatus. Within the scope of the invention, the beam transmitter 1 and the beam receiver 3 can assume different distances from the third mount apparatus 25, so that oblique projections are also possible. However, the beam transmitter 1 and the beam receiver 3 must hereby be mounted pivotably in such a way that the central beam of the beam bundle strikes on the beam receiver 3 as perpendicularly as possible, even in oblique projections. Alternatively, or in addition, the third mount apparatus 25 can permit a displacement on a curved arm 27, so that oblique projections are likewise possible.

Figure 17:
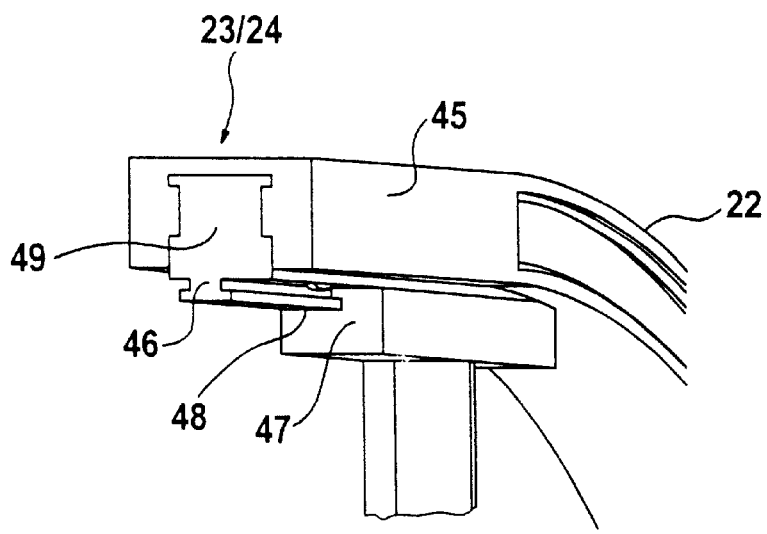
FIG. 17 is a detailed view of a portion of the embodiment according to FIG. 15.

FIG. 17 shows an embodiment the extension 23 (which also applies to the extension 24), wherein the extension 23 is formed by a first segment 45 that is connected with the curved holder 22. In this embodiment, the inner sides of the segment 45 have a region 46 that is fashioned so as to be approximately T-shaped, and that extends at least along the segment 45. A second segment 47 is connected with the beam receiver 3 (or the beam transmitter 2 in the case of the extension 24), and a groove 48 that is approximately T-shaped is fashioned in this second segment 47. The second segment 47 can be displaced, with the beam receiver 3 (or beam transmitter 2) fixed thereto, along the T-shaped region 46 of the first segment 45. For this displacement, a toothed segment (not shown) can be provided on the second segment 47, this toothed segment meshing with a toothed wheel provided on a drive on the first segment 45. Likewise, displacement by hand is possible, in which case a brake is then provided for arresting movement in the desired position.

Figure 18:
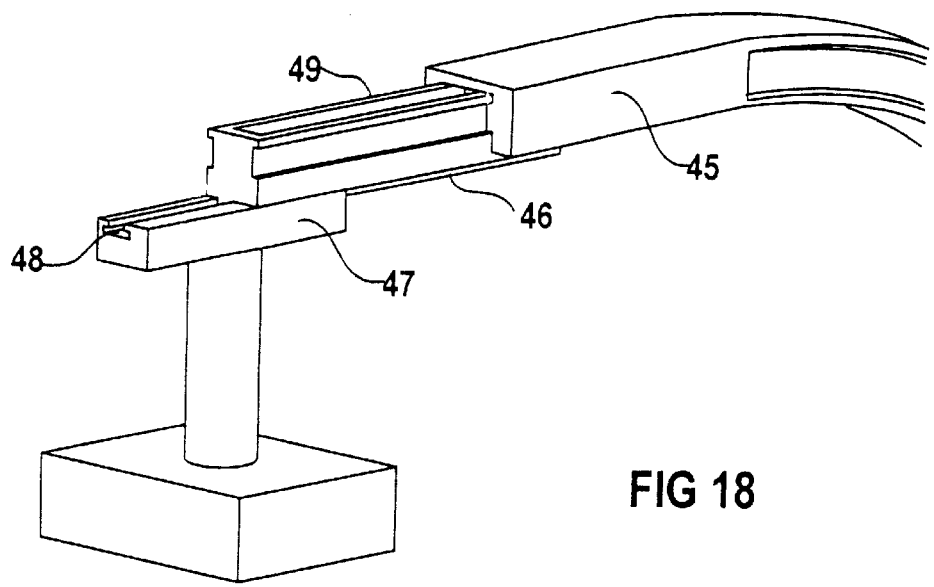
FIGS. 18 and 19 show a detailed views of the embodiment according to FIG. 16.
Figure 19:
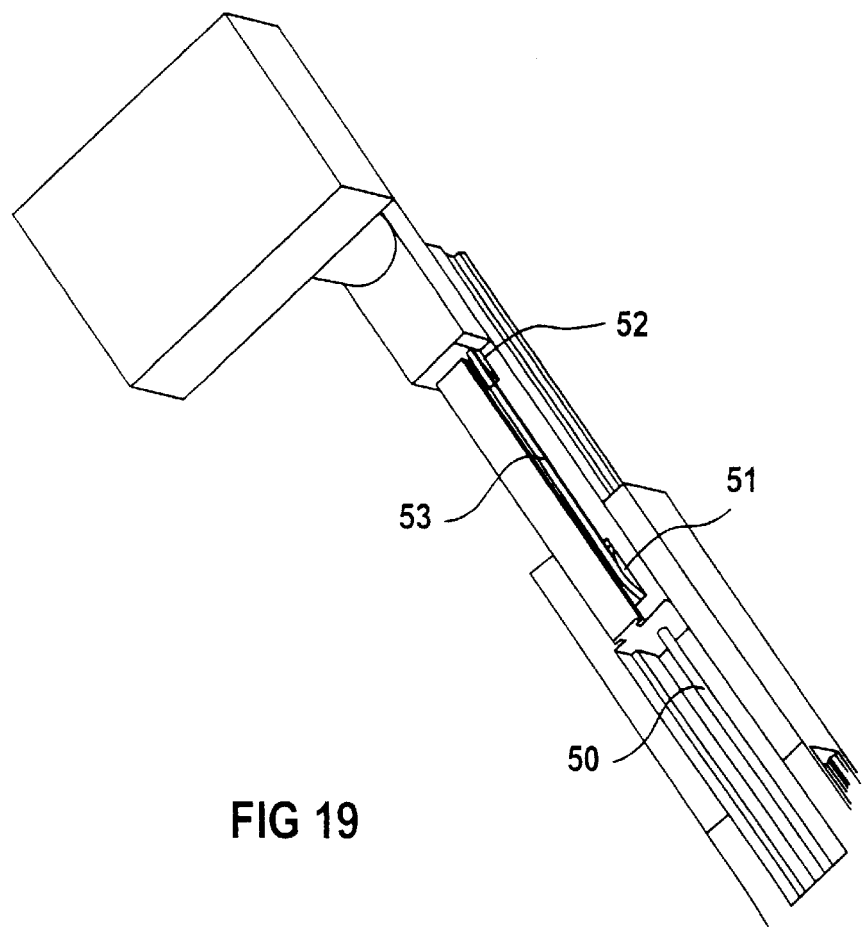

FIGS. 18 and 19 show that a profile part 49 can be displaced on the first segment 45, the T-shaped region 46 being fashioned on this profile part 49. The displacement path for the beam transmitter 2 or for the beam receiver 3 thus is enlarged by approximately the length of the profile part 49. The displacement of the profile part 49 can take place via a spindle 50 controlled by a drive (FIG. 19), the spindle 50 being connected at one end of the part 49 with a first wheel 51 so as to rotate the wheel 51. A second wheel 52 is mounted at the opposite end of the part 49, i.e. at the end farther from the additional curved holder 22, and is connected with the first wheel 51 via a loop-type connecting element 53, e.g. a chain, a cable or a toothed belt. The second segment 47 is coupled with the loop-type connecting element 53, so that during the rotation of the spindle 50 this connecting element 53 is displaced along the profile part 49 and the profile part 49 is simultaneously displaced on the additional curved holder 22. However, for this purpose any other suitable displacement means can be used, e.g. an additional spindle drive or the same spindle drive.

Within the scope of the invention, the first and second circular ring segments 4, 5, as well as the additional curved holder 22, can be of C-shaped construction, with variations being possible with regard to the curve length. In addition, the mount apparatuses 9, 12, 25 can be mounted not only on ceiling rails but also on floor rails, or on a combination of floor and ceiling rails, or exclusively on the floor or on a freely movable carriage.

Although other modifications and changes may be suggested by those skilled in the art, it is the intention of the inventors to embody within the patent warranted hereon all changes and modifications as reasonably and properly come within the scope of their contribution to the art.

We claim as our invention:

1. An X-ray diagnostic apparatus comprising:
   a curved holder;
   an X-ray beam transmitter and an X-ray beam receiver mounted opposite each other on said curved holder, said X-ray beam transmitter and said X-ray beam receiver being operable in a first mode and in a second mode;
   said curved holder, in said first mode, comprising a first circular ring segment on which said X-ray beam transmitter and said X-ray beam receiver are mounted; and
   said curved holder, in said second mode, comprising a second circular ring segment coupled to said first circular ring segment to form a closed ring.

2. An X-ray diagnostic apparatus as claimed in claim 1 wherein said first mode comprises an X-ray transirradiation mode and wherein said second mode comprises an X-ray computed tomography mode.

3. An X-ray diagnostic apparatus as claimed in claim 1 further comprising an energy supply connected to said X-ray beam transmitter and said X-ray beam receiver, and a signal transmission circuit connected to said X-ray beam receiver for transmitting signals produced by said X-ray beam receiver, and a displacement mechanism for rotating said curved holder to rotate said X-ray beam transmitter and said X-ray beam receiver, disposed opposite each other, around a center.

4. An X-ray diagnostic apparatus as claimed in claim 1 further comprising a first mount apparatus on which said first circular ring segment is mounted, and a second mount apparatus on which said second circular ring segment is mounted, said first and second mount apparatuses being displaceable relative to each other to couple and decouple said first and second circular ring segments.

5. An X-ray diagnostic apparatus as claimed in claim 4 wherein said second circular ring segment is mounted to said second mount apparatus so as to be decouplable from said second mount apparatus.

6. An X-ray diagnostic apparatus as claimed in claim 4 wherein at least one of said first mount apparatus and said second mount apparatus is spatially displaceable.

7. An X-ray diagnostic apparatus as claimed in claim 4 wherein said first mount apparatus comprises ceiling rails and a mounting element displaceable along said ceiling rails.

8. An X-ray diagnostic apparatus as claimed in claim 4 wherein said first mount apparatus comprises floor rails and a mounting element displaceable along said floor rails.

9. An X-ray diagnostic apparatus as claimed in claim 4 wherein said first mount apparatus comprises a freely movable carriage.

10. An X-ray diagnostic apparatus as claimed in claim 4 wherein said second mount apparatus comprises ceiling rails and a mounting element displaceable along said ceiling rails.

11. An X-ray diagnostic apparatus as claimed in claim 4 wherein said second mount apparatus comprises floor rails and a mounting element displaceable along said floor rails.

12. An X-ray diagnostic apparatus as claimed in claim 4 wherein said second mount apparatus comprises a freely movable carriage.

13. An X-ray diagnostic apparatus as claimed in claim 1 wherein said second circular ring segment is displaceable relative to said first circular ring segment to form said closed ring.

14. An X-ray diagnostic apparatus as claimed in claim 13 wherein said second circular ring segment is telescopically displaceable on said first circular ring segment.

15. An X-ray diagnostic apparatus as claimed in claim 13 wherein said second circular ring segment is pivotably displaceable around a rotational axis on said first circular ring segment.

* * * * *